(12) United States Patent
Skubsch et al.

(10) Patent No.: US 12,121,600 B2
(45) Date of Patent: Oct. 22, 2024

(54) EMULSION SPRAY

(71) Applicant: BEIERSDORF AG, Hamburg (DE)

(72) Inventors: Kerstin Skubsch, Prisdorf (DE); Kaja Luettig, Hamburg (DE); Claudia Mueller, Tangstedt (DE); Regine Werner, Bienenbuettel (DE)

(73) Assignee: BEIERSDORF AG, Hamburg (DE)

( * ) Notice: Subject to any disclaimer, the term of this patent is extended or adjusted under 35 U.S.C. 154(b) by 928 days.

(21) Appl. No.: 15/516,696

(22) PCT Filed: Sep. 25, 2015

(86) PCT No.: PCT/EP2015/072077
§ 371 (c)(1),
(2) Date: Apr. 4, 2017

(87) PCT Pub. No.: WO2016/055285
PCT Pub. Date: Apr. 14, 2016

(65) Prior Publication Data
US 2017/0290748 A1   Oct. 12, 2017

(30) Foreign Application Priority Data
Oct. 9, 2014 (DE) .......................... 102014220456.9

(51) Int. Cl.
| | |
|---|---|
| *A61K 8/06* | (2006.01) |
| *A61K 8/04* | (2006.01) |
| *A61K 8/44* | (2006.01) |
| *B65D 83/38* | (2006.01) |
| *B65D 83/62* | (2006.01) |

(52) U.S. Cl.
CPC .............. *A61K 8/062* (2013.01); *A61K 8/046* (2013.01); *A61K 8/442* (2013.01); *B65D 83/38* (2013.01); *B65D 83/62* (2013.01)

(58) Field of Classification Search
CPC ........ A61K 8/062; A61K 8/046; A61K 8/442; B65D 83/38; B65D 83/62
See application file for complete search history.

(56) References Cited

U.S. PATENT DOCUMENTS

| | | | | |
|---|---|---|---|---|
| 3,766,085 A | * | 10/1973 | Fahnenstich | A23C 11/04 516/27 |
| 8,857,741 B2 | * | 10/2014 | Morikis | A61K 8/9794 514/642 |
| 9,211,995 B2 | * | 12/2015 | Werner | B65D 33/00 |
| 2005/0238610 A1 | * | 10/2005 | Nielsen | A61K 8/06 424/70.31 |
| 2006/0127344 A1 | * | 6/2006 | Zofchak | A61K 8/06 424/70.31 |
| 2013/0068849 A1 | * | 3/2013 | Birkel | A61Q 5/06 239/1 |
| 2013/0142746 A1 | * | 6/2013 | Demson | A61K 8/345 424/70.1 |
| 2013/0243714 A1 | * | 9/2013 | Kang | A61Q 1/00 424/63 |
| 2014/0186411 A1 | | 7/2014 | Shah et al. | |
| 2015/0352016 A1 | | 12/2015 | Shah et al. | |

FOREIGN PATENT DOCUMENTS

| | | | |
|---|---|---|---|
| DE | 102008021631 A1 | | 10/2009 |
| DE | 102010050774 A1 | | 5/2012 |
| EP | 2783676 A2 | | 10/2014 |
| JP | 2004224706 A | * | 8/2004 |
| JP | 2012206994 A | * | 10/2012 |
| WO | 2010138266 A1 | | 12/2010 |
| WO | 2014105878 A1 | | 7/2014 |
| WO | WO-2014183974 A1 | * | 11/2014 ............. A61Q 17/04 |

OTHER PUBLICATIONS

PubChem, "Isopropyl Palmitate", obtained from the web at https://pubchem.ncbi.nlm.nih.gov/compound/8907#section=Uses&fullscreen=true on Jun. 19, 2020 . (Year: 2020).*
Anonymous: "GNPD—Moisturising Sun Lotion SPF 50+", Aug. 1, 2014 (Aug. 1, 2014) Retrieved from Internet on Oct. 19, 2015: URL:http://www.gnpd.com/sinatra/recordpage/2624935/from search/ZcQBsFUZvR/.
Anonymous: "GNPD—Sun Care Spay", Aug. 1, 2014 (Aug. 1, 2014) Retrieved from Internet on Oct. 19, 2015: URL:http://www.gnpd.comjsinatrajrecordpage/2589939/2589939/from search/ZcQBsFUZvR/.
Anonymous: "Technology: BoV : Bag on Valve system : Aerosols filing : Pump Spray : Bag On Valve", Sep. 9, 2013 (Sep. 9, 2013) Retrieved from Internet on Oct. 19, 2015: URL:https:jjweb.archive.orgjweb/20130909013727/http://www.bagonvalve.comjtechnologyj.

* cited by examiner

*Primary Examiner* — Mina Haghighatian
*Assistant Examiner* — Nathan W Schlientz
(74) *Attorney, Agent, or Firm* — Abel Schillinger, LLP

(57) ABSTRACT

The invention relates to a cosmetic spray consisting of a) an oil-in-water emulsion (O/W emulsion) containing sodium stearoyl glutamate and b) a spray applicator system.

18 Claims, No Drawings

EMULSION SPRAY

BACKGROUND OF THE INVENTION

Field of the Invention

The present invention relates to a cosmetic spray consisting of an oil-in-water emulsion (O/W emulsion) comprising sodium stearoyl glutamate and also a spray applicator system.

The desire to appear beautiful and attractive is naturally rooted in humans. Even if the beauty ideal has changed over the course of time, striving after a flawless appearance has always been the aim of humans. An essential part of a beautiful and attractive appearance is the condition and appearance of the skin.

Discussion of Background Information

Skincare products generally consist of emulsions. Emulsions are generally understood to mean heterogeneous systems which consist of two liquids immiscible, or of only limited miscibility, with each other, which are typically referred to as phases and in which one of the two liquids is dispersed in the form of fine droplets in the other liquid. Externally and with the naked eye, emulsions appear homogeneous.

If the two liquids are water and oil and oil droplets are present finely divided in water, it is an oil-in-water emulsion (O/W emulsion, e.g. milk). The basic character of an O/W emulsion is characterized by the water. In a water-in-oil emulsion (W/O emulsion, e.g. butter), the principle is reversed and the basic character is determined here by the oil.

The abundance of commercially available cosmetic emulsions should not however obscure the fact that these preparations of the prior art have a series of disadvantages.

Particularly when these emulsions are applied directly on to the skin using a spray applicator (e.g. an aerosol can or a bag-on-valve system, see below) from a reservoir under pressure, the problem arises that the preparations on the one hand should be stable to temperature and on storage and not prone to premature phase separation and on the other hand must be sufficiently thin to be sprayable at all.

Furthermore, in these preparations which are released by positive pressure, the problem always arises that the spray mist generated with the aid of a dispenser should have two apparently contradictory properties: on the one hand, the spray mist droplets should be as small as possible and finely dispersed and on the other hand the spray mist should be overall relatively well focused when exiting the system to enable targeted application to defined skin areas. These properties are, of course, influenced firstly by the configuration of the spray head and the dispenser. Secondly however, the composition and its rheological properties also have an influence on the droplet size and the "casting behavior" of the spray mist.

Conventional preparations of the prior art have the disadvantage that the preparations emerge from the applicator system either in the form of a jet ("like a shot from a water pistol"), or that the spray mist is so finely dispersed or so heterogeneous in its droplet size that only a fraction of the preparation reaches the intended target, while a relatively large fraction of the droplets takes a different direction and, inter alfa, sinks prematurely to the ground. This then leads to an undesirable contamination of the application environment with the preparation during the application of the cosmetic.

SUMMARY OF THE INVENTION

It was therefore the object of the present invention to eliminate the deficiencies of the prior art and to develop a cosmetic spray whose spray pattern enables a focused fine spray mist without causing greater "scattering losses". In addition, the sprayed preparation should on striking the skin adhere well thereto and not bounce off it again.

The object, surprisingly, is achieved by a cosmetic spray consisting of
a) an oil-in-water emulsion (O/W emulsion) comprising sodium stearoyl glutamate and also
b) a spray applicator system.

It is preferred according to the invention in this case if the spray applicator system used is a bag-on-valve applicator, in which a bag containing the O/W emulsion is in a pressurized gas container under positive pressure.

In the case of these bag-on-valve systems, the contents of the bag (in this case the O/W emulsion) is pressed outwards by the spray head by the positive pressure in the pressurized gas container on opening the spray head and divided into small droplets ("spray mist") by the dispenser present in the spray head. The pressure compensation therefore does not occur by the direct escape of the pressurized gas from the positive pressure container, but through emptying the contents of the storage bag.

It is advantageous according to the invention if the positive pressure in the pressurized gas container of the bag-on-valve applicator is from 2 to 12 bar (based on the ambient pressure of 1.013 bar).

It is advantageous in accordance with the invention if the spray head of the spray applicator has a uniform spray jet over the entire lifetime of the can. From a distance of 10 cm, a spray pattern of 5-6 cm is favored. If the pressure falls over the entire lifetime of the can, the spray pattern should not exceed 8 cm.

Particularly preferred according to the invention is a spray applicator with the following specification:
9 bar positive pressure with nitrogen
valve DU 2527 or DU 3527 from Aptar®, BOV—cup: Alu gold lacquered—inner gasket: Buna KA 6712—body valve: PP—spring: Inox 302—piston: POM-external gasket: butyl 1.2 mm foil: PET12/ALU8/OPA15/PP75.

According to the invention, advantageous embodiments of the present invention are characterized in that the bag containing the O/W emulsion is formed from a laminate of PE/adhesive/PA/adhesive/AL/adhesive/PET.

In the context of the present invention, it is advantageous if the O/W emulsion according to the invention comprises from 0.1 to 0.5% by weight sodium stearoyl glutamate, based on the total weight of the emulsion.

In the context of the present invention, it is preferred if the O/W emulsion according to the invention comprises from 0.2 to 0.3% by weight sodium stearoyl glutamate, based on the total weight of the emulsion.

According to the invention, it is advantageous if the O/W emulsion according to the invention contains cetearyl alcohol.

If the O/W emulsion contains cetearyl alcohol, it is advantageous according to the invention, if this substance is present in the emulsion at a concentration of from 0.5 to 3% by weight, based on the total weight of the emulsion.

It is advantageous in accordance with the invention if the emulsion contains dicaprylyl ether, isopropyl palmitate and/or shea butter.

If the emulsion contains dicaprylyl ether, it is advantageous in accordance with the invention if this substance is present in this at a concentration of 1 to 7% by weight, based on the total weight of the emulsion.

If the emulsion contains isopropyl palmitate, it is advantageous in accordance with the invention if this substance is present in this at a concentration of 1 to 7% by weight, based on the total weight of the emulsion.

If the emulsion contains shea butter, it is advantageous in accordance with the invention if this substance is present in this at a concentration of 0.5 to 3% by weight, based on the total weight of the emulsion.

According to the invention, advantageous embodiments of the present invention are also characterized in that the emulsion contains dimethicone and/or cyclomethicone.

The oil phase of the emulsion according to the invention may also contain further oil, fat and wax components, for example, polar oils from the group of the lecithins or compounds such as cocoglyceride, caprylic capric triglyceride, olive oil, sunflower oil, jojoba oil, soybean oil, peanut oil, rapeseed oil, almond oil, palm oil, coconut oil, castor oil, wheat germ oil, grape seed oil, safflower oil, evening primrose oil, macadamia nut oil and the like. It is also possible to use compounds such as phenethyl benzoate, 2-phenylethyl benzoate, isopropyl lauroyl sarcosinate, phenyl trimethicone, cyclomethicone, dibutyl adipate, octyl palmitate, octyl cocoate, octyl isostearate, octyldodecyl myristate, octyldodecanol, cetearyl isononanoate, isopropyl myristate, isopropyl stearate, isopropyl oleate, n-butyl stearate, n-hexyl laurate, n-decyl oleate, isooctyl stearate, isononyl stearate, isononyl isononanoate, 2-ethylhexyl palmitate, 2-ethylhexyl laurate, 2-hexyldecyl stearate, 2-octyldodecyl palmitate, stearyl heptanoate, oleyl oleate, oleyl erucate, erucyl oleate, erucyl erucate, tridecyl stearate, tridecyl trimellitate.

Also advantageous in accordance with the invention are, for example, natural waxes of animal and vegetable origin such as beeswax and other insect waxes and berry wax, shea butter and/or lanolin (wool wax).

The oil phase may also be selected advantageously from the group of dialkyl ethers and dialkyl carbonates, e.g. dicaprylyl carbonate, which may be obtained from Cognis for example under the trade name Cetiol CC, are advantageous.

It is also advantageous to select the oil component(s) from the group comprising isoeicosan, neopentyl glycol diheptanoate, propylene glycol dicaprylate/di caprate, caprylic/capric/diglyceryl succinate, butylene glycol dicaprylate/dicaprate, $C_{12-13}$-alkyl lactate, di-$C_{12-13}$-alkyl tartrate, triisostearin, dipentaerythrityl hexacaprylate/hexacaprate, propylene glycol monoisostearate, tricaprylin, dimethyl isosorbide. It is in particular advantageous if the oil phase of the formulations according to the invention has a $C_{12-15}$-alkyl benzoate content.

Any mixtures of such oil and wax components can also be used advantageously in the context of the present invention.

The oil phase can likewise also further comprise advantageously non-polar oils, for example those which are selected from the group of branched and straight-chain hydrocarbons and waxes, especially mineral oil, vaseline (petrolatum), paraffin oil, squalene and squalene, polyolefins, hydrogenated polyisobutenes, C13-16 isoparaffin, C15-19 alkanes and isohexadecane. In terms of polyolefins, the preferred substances are polydecenes.

It is advantageous in accordance with the invention if the emulsion according to the invention contains ethanol and/or glycerol.

If the emulsion contains ethanol, a use concentration of 0.5 to 8% by weight, based on the total weight of the emulsion, is advantageous in accordance with the invention.

If the emulsion contains glycerol, a use concentration of 1 to 12% by weight, based on the total weight of the emulsion, is advantageous in accordance with the invention.

Advantageous embodiments of the present invention are also characterized in that the emulsion contains one or more active ingredients selected from the group of compounds UV filters, magnolia extract, glycyrrhetic acid, urea, arctiin, alpha-lipoic acid, folic acid, phytoene, D-biotin, coenzyme Q10, alpha-glucosylrutin, carnitine, carnosine, caffeine, natural and/or synthetic isoflavonoids, glycerylglucose, creatine, creatinine, taurine, tocopherol, tocopherol acetate, β-alanine and/or licochalcone A.

In accordance with the invention, advantageous UV filters may be selected, for example, from the group of compounds 2-phenylbenzimidazole-5-sulfonic acid and/or salts thereof; phenylene-1,4-bis(2-benzimidazyl)-3,3'-5,5'-tetrasulfonic acid salts; 1,4-di(2-oxo-10-sulfo-3-bornylidenemethyl)benzene and salts thereof; 4-(2-oxo-3-bornylidenemethyl)benzenesulfonic acid salts; 2-methyl-5-(2-oxo-3-bornylidenemethyl)sulfonic acid salts; 2,2'-methylenebis(6-(2H-benzotriazol-2-yl)-4-(1,1,3,3-tetramethylbutyl)phenol); 2-(2H-benzotriazol-2-yl)-4-methyl-6-[methyl-3-[1,3,3,3-tetramethyl-1-[(trimethylsilyl)oxy]disiloxanyl]propyl]phenol; 3-(4-methylbenzylidene)camphor; 3-benzylidenecamphor; ethylhexyl salicylate; terephthalidenedicamphorsulfonic acid; 2-ethylhexyl 2-cyano-3,3-diphenylacrylate; 2-ethylhexyl 4-(dimethylamino)benzoate; amyl 4-(dimethylamino)benzoate; di(2-ethylhexyl) 4-methoxybenzalmalonate; 2-ethylhexyl 4-methoxycinnamate; isoamyl 4-methoxycinnamate; 2-hydroxy-4-methoxybenzophenone, 2-hydroxy-4-methoxy-4'-methylbenzophenone; 2,2'-dihydroxy-4-methoxybenzophenone; homomenthyl salicylate; 2-ethylhexyl 2-hydroxybenzoate; dimethicodiethylbenzalmalonate; 3-(4-(2,2-bis ethoxycarbonylvinyl)phenoxy)propenyl)methoxysiloxane/dimethylsiloxane—copolymer; 4-(tert-butyl)-4'-methoxydibenzoylmethane; hexyl 2-(4'-diethylamino-2'-hydoxybenzoyl)benzoate; dioctylbutylamidotriazone (INCI: Diethylhexyl Butamidotriazone); 2,4-bis [5-1(dimethylpropyl)benzoxazol-2-yl-(4-phenyl)imino]-6-(2-ethylhexyl)imino-1,3,5-triazine with (CAS No. 288254-16-0); 2,4-bis {[4-(2-ethylhexyloxy)-2-hydroxy]phenyl}-6-(4-methoxyphenyl)-1,3,5-triazine (INCI Bis-Ethylhexyloxyphenol Methoxyphenyl Triazine); tris(2-ethylhexyl) 4,4',4"-(1,3,5-tri azine-2,4,6-triyltriimino) trisbenzoate (also: 2,4,6-tris[anilino-(p-carbo-2'-ethyl-1'-hexyloxy)]-1,3,5-triazine (INCI: Ethylhexyl Triazone); 2,4,6-tribiphenyl-4-yl-1,3,5-triazine; merocyanine; titanium dioxide; zinc oxide.

It is advantageous according to the invention if the emulsion contains ethylhexylglycerin, propylene glycol, butylene glycol, 2-methylpropane-1,3-dial, 1,2-pentanediol, 1,2-hexanediol, 1,2-octanediol, piroctone olamine and/or 1,2-decanediol.

In accordance with the invention, advantageous embodiments of the present invention are characterized in that the emulsion contains phenoxyethanol and/or methylparaben. It is advantageous in accordance with the invention if the emulsion is free of propylparaben and butylparaben.

In accordance with the invention, advantageous embodiments are also characterized in that the emulsion comprises at least 70% by weight water, based on the total weight of the emulsion.

DETAILED DESCRIPTION OF EMBODIMENTS OF THE INVENTION

Examples

The following examples are intended to clarify the present invention without limiting it. All quantitative data, fractions and percentages, unless otherwise stated, are specified based on the weight and the total amount or on the total weight of the preparations respectively.

| | A % | B % | C % | D % |
|---|---|---|---|---|
| Sodium stearoyl glutamate | 0.2 | 0.2 | 0.3 | 0.25 |
| Xanthan Gum | | 0.1 | | |
| Carbomer | 0.2 | 0.1 | | |
| Caprylic/Capric Triglyceride | | | 3 | |
| Isopropyl Palmitate | 3.5 | 3.5 | | |
| Shea Butter | 1 | | 1 | |
| Cocoa Butter | | 1 | | |
| Dimethicone | 0.9 | 1 | | |
| Almond oil | | | | 1 |
| Cetearyl Alcohol | 1 | 1 | 1.5 | |
| Dicaprylyl Ether | 2 | | 3 | |
| Glycerol | 7 | 5 | 10 | 8 |
| Aqueous sodium hydroxide solution | pH adjustment | pH adjustment | pH adjustment | pH adjustment |
| Phenoxyethanol | 0.5 | 0.5 | 0.5 | 0.5 |
| Methylparaben | 0.3 | 0.2 | 0.3 | 0.3 |
| Alcohol | 3 | | 2 | 1 |
| Water | to 100 | to 100 | to 100 | to 100 |
| Initial pressure in bar | 7 | 8 | 7 | 8 |
| Pressurized gas | nitrogen | nitrogen | nitrogen | nitrogen |
| Spray valve | DU 3527 | DU 3527 | DU 3527 | DU 3527 |

BOV applicator system, e.g. from Aptar®
Ex-EP BOV cup: Alu gold lacquered—inner gasket: Buna KA 6712—body valve: PP—spring: Inox 302—piston: POM—external gasket: butyl 1.2 mm foil: PET12/ALU8/OPA15/PP75

What is claimed is:

1. A cosmetic spray, wherein the spray consists of
(a) an oil-in-water (O/W) emulsion comprising, based on a total weight of the emulsion, at least 70% by weight of water and (i) from 0.2% to 0.3% by weight of sodium stearoyl glutamate, either alone or in combination with isopropyl palmitate, as the only emulsifier(s) present in the emulsion; (ii) from 5% to 12% by weight of glycerol; and one or more of (iii) from 0.5% to 3% by weight of cetearyl alcohol; (iv) 1% to 7% by weight of isopropyl palmitate; (v) 0.5% to 3% by weight of shea butter; (vi) 1% to 7% by weight of dicaprylyl ether; and (vii) from 0.5% to 8% by weight of ethanol; and
(b) a spray applicator system, and wherein the emulsion does not contain UV filters.

2. The cosmetic spray of claim 1, wherein the spray applicator system is a bag-on-valve applicator system, in which a bag containing the O/W emulsion is present in a pressurized gas container under positive pressure.

3. The cosmetic spray of claim 2, wherein a spray head of the spray applicator system exhibits a uniform spray jet over an entire lifetime of the cosmetic spray.

4. The cosmetic spray of claim 1, wherein the emulsion comprises at least (iii).

5. The cosmetic spray of claim 1, wherein the emulsion comprises at least (iv).

6. The cosmetic spray of claim 1, wherein the emulsion comprises at least (v).

7. The cosmetic spray of claim 1, wherein the emulsion comprises at least (vi).

8. The cosmetic spray of claim 1, wherein the emulsion comprises at least (vii).

9. The cosmetic spray of claim 1, wherein the emulsion comprises at least two of (iii), (iv), (v), (vi) and (vii).

10. The cosmetic spray of claim 1, wherein the emulsion comprises at least three of (iii), (iv), (v), (vi) and (vii).

11. The cosmetic spray of claim 10, wherein the O/W emulsion further comprises dimethicone and/or cyclomethicone.

12. The cosmetic spray of claim 1, wherein the emulsion comprises at least four of (iii), (iv), (v), (vi) and (vii).

13. The cosmetic spray of claim 1, wherein the emulsion comprises all of (iii), (iv), (v), (vi) and (vii).

14. The cosmetic spray of claim 1, wherein the O/W emulsion further comprises dimethicone and/or cyclomethicone.

15. The cosmetic spray of claim 1, wherein the emulsion further comprises one or more active ingredients selected from magnolia bark extract, glycyrrhetic acid, urea, arctiin, alpha-lipoic acid, folic acid, phytoene, D-biotin, coenzyme Q10, alpha-glucosylrutin, carnitine, carnosine, caffeine, natural and synthetic isoflavonoids, glycerylglucose, creatine, creatinine, taurine, tocopherol, tocopherol acetate, ß-alanine, and licochalcone A.

16. The cosmetic spray of claim 1, wherein the O/W emulsion further comprises one or more of 1,2-pentanediol, 1,2-hexanediol, 1,2-octanediol, and 1,2-decanediol.

17. The cosmetic spray of claim 1, wherein the O/W emulsion further comprises phenoxyethanol and/or methylparaben and is free of propylparaben and butylparaben.

18. The cosmetic spray of claim 17, wherein the O/W emulsion comprises phenoxyethanol and methylparaben.

* * * * *